United States Patent
Garrison et al.

(10) Patent No.: US 10,095,981 B1
(45) Date of Patent: Oct. 9, 2018

(54) MULTI-STATE QUANTUM OPTIMIZATION ENGINE

(71) Applicant: Accenture Global Solutions Limited, Dublin (IE)

(72) Inventors: Daniel Garrison, Washington, MI (US); Andrew E. Fano, Lincolnshire, IL (US); Jurgen Albert Weichenberger, Surrey (GB)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 15/466,342

(22) Filed: Mar. 22, 2017

(51) Int. Cl.
*G06N 99/00* (2010.01)

(52) U.S. Cl.
CPC ......... *G06N 99/002* (2013.01); *G06N 99/005* (2013.01)

(58) Field of Classification Search
None
See application file for complete search history.

(56) References Cited

PUBLICATIONS

Hogg, Tad, and Dmitriy Portnoy. "Quantum optimization." Information Sciences 128.3 (2000): 181-197.*
Bapst, Victor, et al. "The quantum adiabatic algorithm applied to random optimization problems: The quantum spin glass perspective." Physics Reports 523.3 (2013): 127-205.*
Adachi, Steven H., and Maxwell P. Henderson. "Application of quantum annealing to training of deep neural networks." arXiv preprint arXiv:1510.06356 (2015).*
Farhi, Edward, et al. "Quantum computation by adiabatic evolution." arXiv preprint quant-ph/0001106 (2000).*
Liu, Pu, and B. J. Berne. "Quantum path minimization: An efficient method for global optimization." The Journal of Chemical Physics 118.7 (2003): 2999-3005.*
Roland, Jeremie, and Nicolas J. Cerf. "Quantum search by local adiabatic evolution." Physical Review A 65.4 (2002): 042308.*
Steffen, Matthias, et al. "Experimental implementation of an adiabatic quantum optimization algorithm." Physical Review Letters 90.6 (2003): 067903.*
Wiebe, Nathan, Ashish Kapoor, and Krysta M. Svore. "Quantum deep learning." arXiv preprint arXiv:1412.3489 (2014).*
'adl. stanford.edu' [online]. "Chapter 5—Constrained Optimization," Apr. 26, 2012 [retrieved on Aug. 28, 2017], Retrieved from the Internet: URL <http://adl.stanford.edu/aa222/Lecture_Notes_files/chapter5_contrainopt.pdf> . 20 pages.

(Continued)

*Primary Examiner* — Kakali Chaki
*Assistant Examiner* — Daniel Pellett
(74) *Attorney, Agent, or Firm* — Fish & Richardson P.C.

(57) ABSTRACT

Methods, systems, and apparatus for solving optimization tasks. In one aspect, a method includes receiving input data comprising (i) data specifying an optimization task to be solved, and (ii) data specifying task objectives for solving the optimization task, comprising one or more local task objectives and one or more global task objectives; processing the received input data to obtain one or more initial solutions to the optimization task based on the local task objectives, wherein at least one initial solution is obtained from a first quantum computing resource; and processing the generated one or more initial solutions using a second quantum computing resource to generate a global solution to the optimization task based on the global task objectives.

21 Claims, 5 Drawing Sheets

(56) References Cited

PUBLICATIONS

'arxiv.org' [online]. "Quantum Computation by Adiabatic Evolution," Jan. 28, 2000 [retrieved on Aug. 28, 2017]. Retrieved from the Internet: URL: https://arxiv.org/abs/quant-ph/0001106. 24 pages.

* cited by examiner

MULTI-STATE QUANTUM OPTIMIZATION ENGINE

BACKGROUND

An optimization task is a task of finding a best solution to a problem from all feasible solutions to the problem. To perform an optimization task, quantum hardware, e.g., a quantum computing device, may be constructed and programmed to encode the solution to a corresponding machine optimization problem into an energy spectrum of a many-body quantum Hamiltonian characterizing the quantum hardware. For example, the solution is encoded in the ground state of the Hamiltonian.

SUMMARY

This specification relates to solving optimization tasks using a multi-state quantum optimization engine. The optimization engine generates solutions to optimization tasks by making nested calls to multiple quantum computing devices. A first call to a quantum computing device may be performed to generate one or more local solutions to the optimization task. A second call to a quantum computing device may be performed to generate a global solution to the optimization task that is based on the generated one or more local solutions.

In general, one innovative aspect of the subject matter described in this specification can be implemented in a method for solving an optimization task using a system including multiple computing resources, wherein the multiple computing resources comprise at least one quantum computing resource, the method including the actions of receiving input data comprising (i) data specifying the optimization task to be solved, and (ii) data specifying task objectives for solving the optimization task, comprising one or more local task objectives and one or more global task objectives; processing the received input data to obtain one or more initial solutions to the optimization task based on the local task objectives, wherein at least one initial solution is obtained from a first quantum computing resource; and processing the generated one or more initial solutions using a second quantum computing resource to generate a global solution to the optimization task based on the global task objectives.

Other implementations of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination. In some implementations the method further comprises comparing the generated global solution to the optimization task with the global task objectives to determine whether the generated global solution sufficiently satisfies the global task objectives.

In some implementations the method further comprises, in response to determining that the generated global solution sufficiently satisfies the global task objectives, providing as output data representing the one or more initial solutions to the optimization task.

In some implementations the method further comprises, in response to determining that the generated global solution does not sufficiently satisfy the global task objectives: generating modified input data comprising (i) data specifying the optimization task to be solved, and (ii) modified local task objectives for solving the optimization task; processing the received modified input data to obtain one or more modified solutions to the optimization task based on the modified local task objectives; and processing the generated one or more modified solutions using the second quantum computing resource to generate a modified global solution to the optimization task based on the global task objectives.

In some implementations generating modified input data comprises applying deep learning regularization techniques to the received input data to generate biased input data.

In some implementations processing the received input data to generate one or more initial local solutions to the optimization task comprises: partitioning the optimization task into one or more sub-tasks; and for each sub-task: identifying local task objectives relevant to the sub-task; routing (i) the sub-task, and (ii) the identified local task objectives to respective computing resources included in the system; and obtaining a respective solution to the sub-tasks from the respective computing resources included in the system.

In some implementations partitioning the optimization task into one or more sub-tasks comprises representing the optimization task as a graph and partitioning the graph into minimally connected sub graphs.

In some implementations processing the generated one or more initial local solutions to obtain a global solution to the optimization task based on the global task objectives further comprises processing the generated one or more initial local solutions and additional data comprising one or more of (i) data representing obtained global solutions to previously received optimization tasks within a predetermined time frame, (ii) data representing a forecast of future received optimization tasks within a remaining predetermined time frame, (iii) data representing a solution to the optimization task that is independent of the global task objectives, to obtain the global solution to the optimization task based on the global task objectives.

In some implementations the second quantum computing resource is a quantum annealer.

In some implementations the global solution to the optimization task based on the global task objectives is encoded into an energy spectrum of a problem Hamiltonian characterizing the quantum annealer.

In some implementations processing the generated one or more initial local solutions to obtain a global solution to the optimization task comprises performing a quantum annealing schedule task based on at least the data representing a forecast of future received optimization tasks within a remaining predetermined time frame.

In some implementations processing the received input data to obtain one or more initial solutions to the optimization task based on the local task objectives comprises performing a first set of algorithms; processing the generated one or more initial solutions using a second quantum computing resource to generate a global solution to the optimization task based on the global task objectives comprises performing a second set of algorithms; and the first set of algorithms is different to the second set of algorithms.

In some implementations the initial solutions to the optimization task comprise probabilistic solutions to the optimization task.

In some implementations the received input data specifying task objectives for solving the optimization task comprise static data and real-time data.

In some implementations the multiple computing resources comprise one or more of (i) quantum gate computers, (ii) quantum annealers, or (iii) quantum simulators.

The subject matter described in this specification can be implemented in particular ways so as to realize one or more of the following advantages.

For some optimization tasks, quantum computing devices may offer an improvement in computational speed compared to classical devices. For example, quantum computers may achieve an improvement in speed for tasks such as database search or evaluating NAND trees. As another example, quantum annealers may achieve an improvement in computational speed compared to classical annealers for some optimization tasks. For example, determining a global minimum or maximum of a complex manifold associated with the optimization task is an extremely challenging task. In some cases, using a quantum annealer to solve an optimization task can be an accurate and efficient alternative to using classical computing devices.

A multi-state quantum optimization engine, as described in this specification, uses nested calls to quantum computing devices to solve optimization tasks. The multi-state quantum optimization engine uses both classical and quantum computing devices, increasing the computational capabilities of the optimization engine compared to optimization engines that do not include both classical and quantum computing devices. In addition, by using nested calls to quantum computing devices, the multi-state quantum optimization engine may iteratively determine one or more local solutions to the optimization task that, together, achieve one or more global objectives of the optimization task. Such local solutions may be used to perform actions on a system defining the optimization task, improving the efficiency and/or cost effectiveness of the system. Furthermore, by incorporating dynamic input data, the multi-state quantum optimization engine may generate global or local solutions to an optimization task that are relevant and effective in real-time.

A multi-state quantum optimization engine, as described in this specification, may be used to solve optimization tasks from a wide range of applications, including but not limited to machine learning, sampling/Monte Carlo, information security, pattern recognition, image analysis, systems design, precision agriculture, scheduling, network design and bioinformatics. In addition, the multi-state quantum optimization engine may be used to provide complex real-time recommendation support.

Typically, the number of variables that can be efficiently described by a purely classical multi-state system is restricted. The multi-state quantum optimization engine, as described in this specification, combines quantum technology with classical technology in such a manner that allows the system to describe an increased number of variables compared to a classical multi-state system. In addition, the multi-state quantum optimization engine may apply spherical description of computational tasks and apply multi-shell projections from the core of the sphere towards the surface. Therefore, solutions to computational tasks generated by the multi-state quantum optimization engine may be more accurate than solutions generated by a classical multi-state optimization system. In addition, the multi-state quantum optimization engine may be applied to a wider range of computational tasks than a classical multi-state system.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system and method for performing optimization tasks, e.g., optimization tasks, using nested calls to one or more quantum computing devices. The quantum computing devices include quantum annealers, and optionally quantum simulators or quantum gate computers. The system receives input data specifying an optimization task to be solved and corresponding task objectives. A first set of calls to a set of computing devices including at least one quantum computing device obtains a set of initial local solutions to the optimization task, e.g., locally optimal solutions. Based on the set of initial local solutions, a second set of calls to the computing devices, in particular to a quantum annealer, obtains a solution to the optimization task, e.g., a globally optimal solution.

In some cases, an obtained solution may be compared to global task objectives, e.g., global targets, for the optimization task. If the obtained solution sufficiently satisfies the global task objectives, corresponding initial solutions may be used to determine one or more actions to be taken, e.g., adjustments to optimization task parameters. If the obtained solution does not sufficiently satisfy the global task objectives, the system may iteratively repeat the process of obtaining a solution to the optimization task based on modified input data until a solution that sufficiently satisfies the global task objectives is obtained.

Example Operating Environment

Figure 1A:
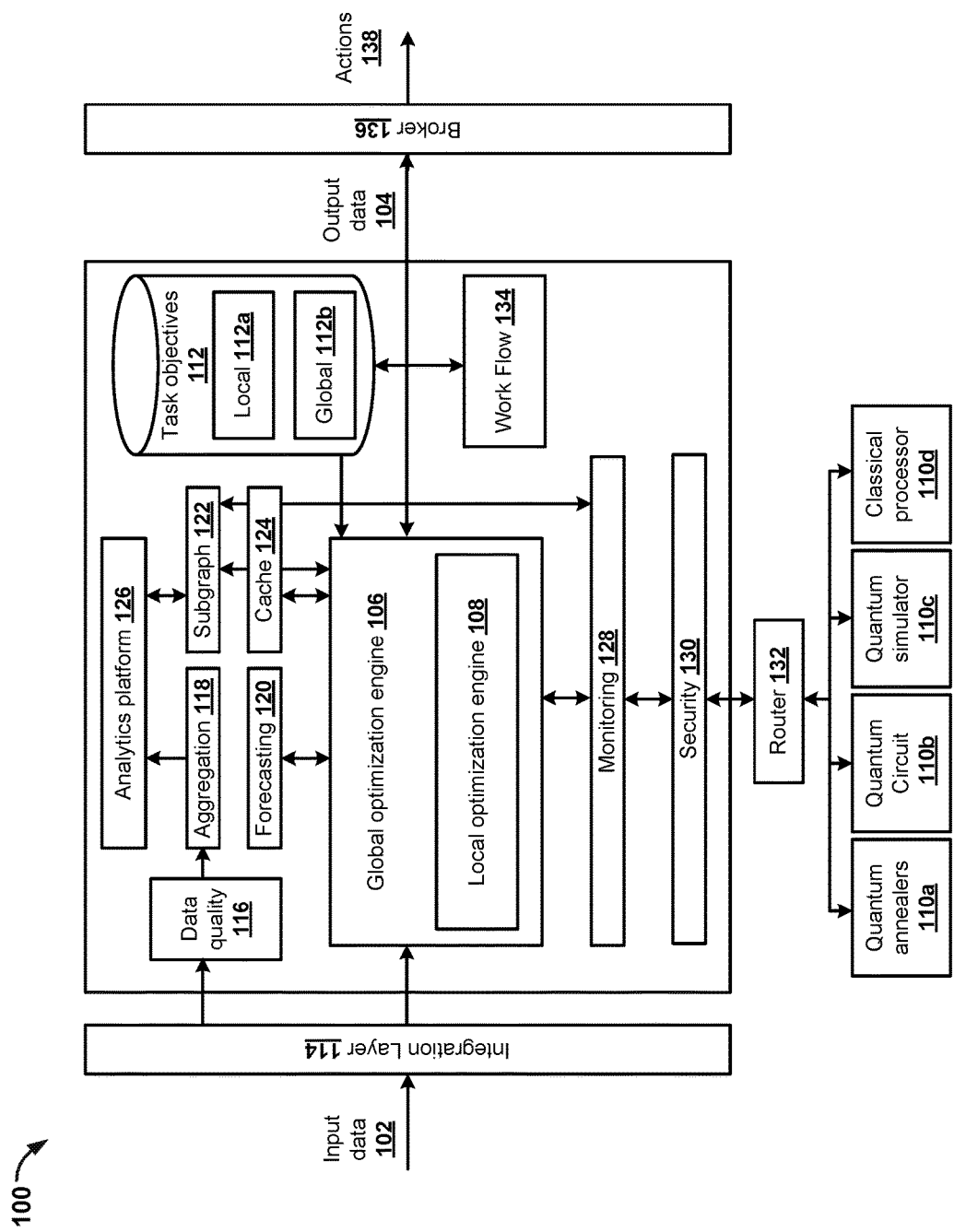
FIG. 1A depicts an example multi-state quantum optimization engine.

FIG. 1A depicts an example multi-state quantum optimization engine 100. The multi-state quantum optimization engine 100 is an example of a system implemented as computer programs on one or more classical or quantum computing devices in one or more locations, in which the systems, components, and techniques described below can be implemented. Components of the multi-state quantum optimization engine 100 may be interconnected by a digital and/or quantum data communication network.

The multi-state quantum optimization engine 100 is configured to receive as input data representing an optimization task to be solved, e.g., input data 102. For example, in some cases the multi-state quantum optimization engine 100 may be configured to solve multiple optimization tasks, and the input data 102 may be data that specifies one of the multiple optimization tasks. The input data 102 representing the optimization task to be solved may specify one or more properties of the optimization task, parameters associated with the optimization task, e.g., parameters over which an objective function representing the optimization task is to be optimized, and one or more values of the parameters. In some cases the input data 102 may include static input data and dynamic input data, e.g., real-time input data.

For example, the input data 102 may be data that represents the task of optimizing the design of a water network, e.g., to improve the amount of water delivered by the network, or to reduce the amount of water wastage in the network. In this example, the input data 102 may include static input data representing one or more properties of the water network, e.g., a total number of available water pipes, a total number of available connecting nodes or a total number of available water tanks. In addition, the input data 102 may include data representing one or more parameters associated with the optimization task, e.g., level of water pressure in each pipe, level of water pressure at each connecting node, height of water level in each water tank, concentration of chemicals in the water throughout the network, water age or water source. Furthermore, the input data 102 may include dynamic input data representing one or more current properties or values of parameters of the water network, e.g., a current number of water pipes in use, a current level of water pressure in each pipe, a current concentration of chemicals in the water, or a current temperature of the water.

In some implementations, the input data 102 may further include data specifying one or more task objectives associated with the optimization task. The task objectives may include local task objectives and global task objectives. Local task objectives may include local targets to be considered when solving the optimization task, e.g., local objectives of a solution to the optimization task. For example, local objectives may include constraints on values of subsets of optimization task variables. Global task objectives may include global targets to be considered when solving the optimization task, e.g., global objectives of a solution to the optimization task.

For example, continuing the above example of the task of optimizing a water network, the input data 102 may further include data specifying local task objectives such as a constraint on the concentration of chemicals in the water, e.g., constraining the chemical concentration to between 0.2% and 0.5%, and on the number of water pipes in use, e.g., constraining the total number of water pipes to less than 1000. Another example local task objective may be to optimize a particular portion of the water network. In addition, the input data 102 may further include data specifying global task objectives such as one or more global targets, e.g., a target of keeping water wastage to below 2% or a target of distributing at least 10 million gallons of water per day.

In other implementations, data specifying one or more task objectives associated with the optimization task may be stored in the multi-state quantum optimization engine 100, e.g., in task objective data store 112. For example, as described above, the multi-state quantum optimization engine 100 may be configured to solve multiple optimization tasks and the input data 102 may be data that specifies one of the multiple optimization tasks. In this example, the multi-state quantum optimization engine 100 may be configured to store task objectives corresponding to each optimization task that it is configured to perform. For convenience, data specifying one or more task objectives associated with the optimization is described as being stored in task objective data store 112 throughout the remainder of this document.

The multi-state quantum optimization engine 100 is configured to process the received input data 102 to generate output data 104. In some implementations, the generated output data 104 may include data representing a global solution to the optimization task specified by the input data 102, e.g., a global solution to the optimization task based on one or more global task objectives 112b. Processing received input data representing an optimization task to be solved and one or more objectives for solving the optimization task to generate output data representing a global solution to the optimization task is described in more detail below with reference to FIGS. 2 and 3.

Figure 1B:
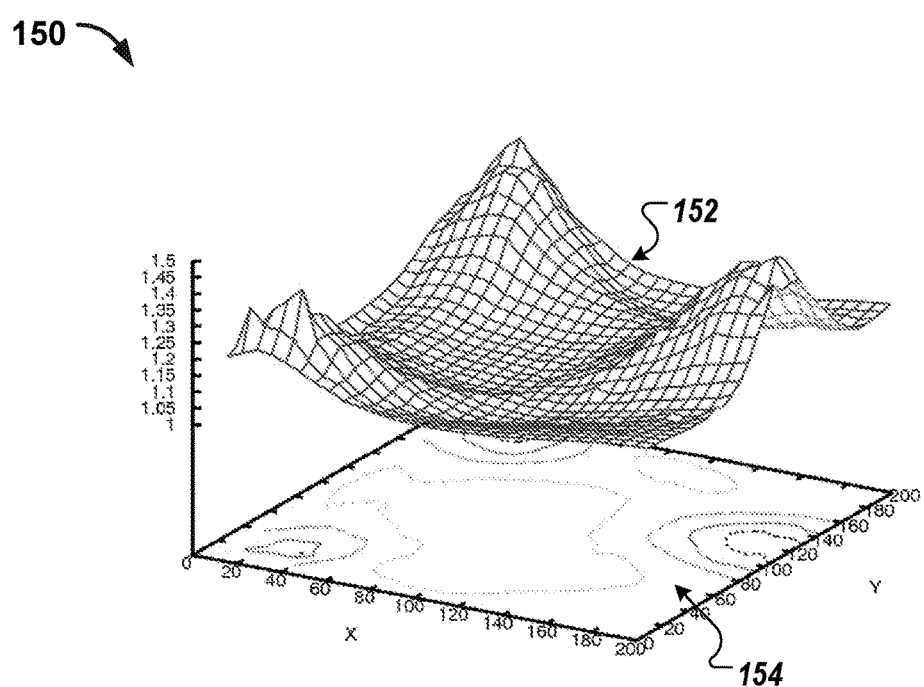
FIG. 1B depicts an example visualization of a global search space and local search space.

In other implementations or in addition, the output data 104 may include data representing one or more local solutions to the optimization task, e.g., one or more initial solutions to the optimization task that are based on local task objectives 112a and global task objectives 112b. Local solutions to the optimization task may include solutions to sub-tasks of the optimization task. For example, local solutions may include solutions that are optimal over a subset of the parameters associated with the optimization task, e.g., where the subset is specified by the local task objectives 112a. That is, local solutions may include solutions that are optimal over a subspace, or local space, of a global search space of the optimization task. For example, a local space may be the result of a projection of a multi-dimensional spline representing the global search space to a two-dimensional base space. An example visualization 150 of a global search space and local space is shown in FIG. 1B. In FIG. 1B, multi-dimensional spline 152 represents a global search space, and two-dimensional base space 154 represents a local space.

As another example, in cases where the optimization task is a separable task, e.g., a task that may be written as the sum of multiple sub-tasks, local solutions may include optimal solutions to each of the sub-tasks in the sum of sub-tasks, e.g., where the sub-tasks are specified by the local task objectives 112a. Generating one or more local solutions to an optimization task based on one or more local and global task objectives is described in more detail below with reference to FIG. 4.

For example, continuing the above example of the task of optimizing a water network, the output data 104 may include data representing a globally optimal configuration (with respect to global task objectives, e.g., wastage targets and productivity targets) of the above described parameters associated with the water network optimization task. Alternatively or in addition, the output data 104 may include data representing multiple local solutions to the water network optimization task, e.g., data specifying an optimal number of water pipes to use, an associated water pressure in each pipe, or a concentration of chemicals in the water flowing through the network. In some implementations, parameter values specified by local solutions may be the same as parameter values specified by a global solution. In other implementations, parameter values specified by local solutions may differ from parameter values specified by a global solution, e.g., a local solution may suggest a chemical concentration of 0.4%, whereas a global solution may suggest a chemical concentration of 0.3%.

The output data 104 may be used to initiate one or more actions associated with the optimization task specified by the input data 102, e.g., actions 138. For example, continuing the above example of the task of optimizing a water network, the output data 104 may be used to adjust one or more parameters in the water network, e.g., increase or decrease a current water chemical concentration, increase or decrease a number of water pipes in use, or increase or decrease one or more water pipe pressures.

Optionally, the multi-state quantum optimization engine 100 may include an integration layer 114 and a broker 136. The integration layer 114 may be configured to manage received input data, e.g., input data 102. For example, the integration layer 114 may manage data transport connectivity, manage data access authorization, or monitor data feeds coming into the system 100.

The broker 136 may be configured to receive output data 104 from the multi-state quantum optimization engine and to generate one or more actions to be taken, e.g., actions 138. The actions may include local actions, e.g., adjustments to a subset of optimization parameters, which contribute towards achieving local and global targets of the optimization task, as described in more detail below with reference to FIG. 4.

The multi-state quantum optimization engine 100 includes a global optimization engine 106, which in turn includes a local optimization engine 108. The global optimization engine 106 is configured to receive the input data 102 and task objectives 112 for the optimization task specified by the input data 102, and to provide the input data 102 and one or more local task objectives 112a to the local optimization engine 108.

The local optimization engine 108 is configured to process the received data to obtain one or more initial solutions to the optimization task based on the one or more local task objectives 112a, e.g., one or more local solutions to the optimization task.

In some implementations, the local optimization engine 108 may be configured to process received data using one or more computing resources included in the local optimization engine 108 or otherwise included in the multi-state quantum optimization engine 100. In other implementations, the local optimization engine may be configured to process received data using one or more external computing resources, e.g., additional computing resources 110a-110d. For example, the local optimization engine 108 may be configured to analyze the received input data 102 representing the optimization task to be solved and the data representing corresponding local task objectives 112a, and outsource one or more computations associated with solving the optimization task based on the local task objectives 112a to the additional computing resources 110a-110d.

The additional computing resources 110a-110d may include multiple quantum annealer computing resources, e.g., quantum annealers 110a. A quantum annealer is a device configured to perform quantum annealing—a procedure for finding the global minimum of a given objective function over a given set of candidate states using quantum tunneling. Quantum tunneling is a quantum mechanical phenomenon where a quantum mechanical system overcome localized barriers in the energy landscape which cannot be overcome by classically described system. An example quantum annealer is described in more detail below with reference to FIG. 2.

The additional computing resources 110a-110d may include one or more quantum gate processors, e.g., quantum gate processor 110b. A quantum gate processor includes one or more quantum circuits, i.e., models for quantum computation in which a computation is performed using a sequence of quantum logic gates, operating on a number of qubits (quantum bits).

The additional computing resources 110a-110d may include one or more quantum simulators, e.g., quantum simulator 110c. A quantum simulator is a quantum computer that may be programmed to simulate other quantum systems and their properties. Example quantum simulators include experimental platforms such as systems of ultracold quantum gases, trapped ions, photonic systems or superconducting circuits.

The additional computing resources 110a-110d may include one or more classical processors, e.g., classical processor 110d. In some implementations, the one or more classical processors, e.g., classical processor 110d, may include supercomputers, i.e., computers with high levels of computational capacity. For example, the classical processor 110d may represent a computational system with a large number of processors, e.g., a distributed computing system or a computer cluster.

The multi-state quantum optimization engine 100 includes a router 132 that is configured to determine which, if any, computations to outsource to the additional computing resources 110a-110d. Determining which, if any, computations to outsource to the additional computing resources 110a-110d is dependent on multiple factors, including the type of computations, current availability of the additional computing resources 110a-110d, cost of running the additional computing resources 110a-110d, and the type of optimization task. For example, in some cases an additional computing resource may be configured to perform only a limited number of specific optimization tasks or types of optimization tasks.

Optionally, the multi-state quantum optimization engine 100 may include a monitoring module 128. The monitoring module 128 is configured to monitor interactions between and transactions to and from the one or more additional computing resources 110a-d. For example, the monitoring module 128 may be configured to detect failed or stuck calls to one or more of the additional computing resources 110a-d. Example failures that can cause a call to one or more of the additional computing resources 110a-d to fail or get stuck include issues with a transport layer included in the system 100, i.e., issues with data being moved through the cloud, security login failures, or issues with the additional computing resources 110a-d themselves such as performance or availability of the additional computing resources 110a-d. The monitoring module 128 may be configured to process detected failed or stuck calls to one or more of the additional computing resources 110a-d and determine one or more corrective actions to be taken by the system 100 in response to the failed or stuck calls. Alternatively, the monitoring module 128 may be configured to notify other components of the system 100, e.g., the global optimization engine 106 or router 132, of detected failed or stuck calls to one or more of the additional computing resources 110a-d.

For example, if one or more computations are outsourced to a particular quantum computing resource, and the particular quantum computing resource suddenly becomes unavailable or is processing outsourced computations too slowly, the monitoring module 128 may be configured to notify relevant components of the system 100, e.g., the router 132 or global optimization engine 106. The monitoring system 128 may be further configured to provide the relevant components of the system with a suggested corrective action, e.g., instructing the system 100 to outsource the computation to a different computing resource or to retry the computation using the same computing resource. Generally, the suggested corrective actions may include actions that keep the system 100 successfully operating in real time, e.g., even when resource degradations outside of the system 100 are occurring.

Optionally, the multi-state quantum optimization engine 100 may include a security component 130. The security component 130 may be configured to perform operations relating to the security of the system 100. Example operations include, but are not limited to, preventing system intrusions, detecting system intrusions, providing authentication to external systems, encrypting data received by and output by the system 100, and preventing and/or remedying denial of service (DoS).

The local optimization engine 108 is configured to provide the one or more obtained initial solutions to the optimization task to the global optimization engine 106. The global optimization engine 106 is configured to process the received one or more initial solutions to the optimization task using a quantum computing resource to generate a global solution to the optimization task based on the global task objectives 112b. Generating a global solution to an optimization task based on one or more initial solutions to the optimization task and on one or more global task objectives is described in more detail below with reference to FIGS. 2, 3 and 4.

Optionally, the multi-state quantum optimization engine 100 may include a subgraph module 122. The subgraph module 122 may be configured to partition an optimization task into multiple sub-tasks. For example, the subgraph module 122 may be configured to analyze data specifying an optimization task to be solved, and to map the optimization task to multiple minimally connected subgraphs. The minimally connected subgraphs may be provided to the global optimization engine for processing, e.g., such processing may involve providing the subgraphs to the additional computing resources 110a-110d.

Optionally, the multi-state quantum optimization engine 100 may include a cache 124. The cache 124 is configured to store previously generated initial solutions and global solutions to optimization tasks that the multi-state quantum optimization engine has previously been used to solve. In some cases this may include initial and global solutions to a same optimization task, e.g., with different task objectives or different dynamic input data. In other cases this may include initial and global solutions to different optimization tasks. The cache 124 may be configured to store previously generated initial solutions and global solutions to previously received optimization tasks from a specified time frame of interest, e.g., initial and global solutions generated within the last 24 hours. The cache may store the initial and global solutions with a corresponding label that identifies the optimization task to which the solutions belong, the task objectives associated with the initial and global solutions, and the system input data associated with the optimization task.

During operation, the global optimization engine 106 and local optimization engine 108 may be configured to query the cache 124 to determine whether existing initial or global solutions to a received optimization task with corresponding task objectives exists in the cache. If it is determined that existing initial or global solutions do exist, the local optimization engine and global optimization engine may retrieve the solutions and provide the solutions directly as output, e.g., as output data 104. If it is determined that existing initial or global solutions do not exist, the local optimization engine 106 and global optimization engine 108 may process the received data as described above.

In some implementations, the system 100 may be configured to determine whether a solution to a similar optimization task is stored in the cache 124. For example, the system 100 may be configured to compare a received optimization task to one or more other optimization tasks, e.g., optimization tasks that have previously received by the system 100, and determine one or more respective optimization task similarity scores. If one or more of the determined similarity scores exceed a predetermined similarity threshold, the system 100 may determine that the optimization task is similar to another optimization task, and may use a previously obtained solution to the optimization task as an initial solution to the optimization task, or as a final solution to the optimization task. In some cases similarity thresholds may be predetermined as part of an initial learning and parameter configuration process.

Optionally, the multi-state quantum optimization engine 100 may include a forecasting module 120. The forecasting module 120 forecasts future global solutions and their impact on data entering the system 100, e.g., their impact on future input data 102. In some implementations the forecasting module 120 may be configured to forecast future global solutions within a remaining time of a particular time frame of interest, e.g., for the next 10 hours of a current 24 hour period.

For example, the forecasting module 120 may include forecast data from historical periods of time. Forecast data may be compared to current conditions and optimization task objectives to determine whether a current optimization task and corresponding task objectives are similar to previously seen optimization tasks and corresponding task objectives. For example, the system 100 may include forecast data for a period of interest, e.g., a 24 hour period of interest on a particular day of the week. In this example, on a similar day of the week at a later time, the system 100 may use forecast data for the period of interest to determine whether conditions and optimization task objectives for the current period of interest is similar to the conditions and optimization task objectives for the previous period of interest. If it is determined that the conditions and optimization task objectives for the current period of interest is similar to the conditions and optimization task objectives for the previous period of interest, the system 100 may leverage previous results of previously seen optimization tasks as future forecast data points until the forecast data points are replaced by real results from current calculations.

As another example, the forecasting module 120 may be configured to receive real time input data that may be used to forecasts future global solutions and their impact on data entering the system 100. For example, current weather conditions may be used to forecast future global solutions to optimization tasks related to water network optimization or precision agriculture.

Optionally, the multi-state quantum optimization engine 100 may include a data quality module 116. The data quality module 116 is configured to receive the input data 102 and to analyze the input data 102 to determine a quality of the input data 102. For example, the data quality module 116 may score the received input data 102 with respect to one or more data quality measures, e.g., completeness, uniqueness, timeliness, validity, accuracy or consistency. For example, in some implementations the system 100 may be configured to receive a data feed from an internet of things (IoT) sensor, e.g., that tracks the position of an object or entity within an environment. If the data quality module 116 determines that one of these objects or entities has moved an unrealistic distance in a particular period of time, the data quality module 116 may determine that the quality of the received data feed is questionable and that the data feed may need to be further analyzed or suspended.

Each measure may be associated with a respective predetermined score threshold that may be used to determine whether data is of acceptable quality or not. For example, the data quality module 116 may determine that the input data 102 is of an acceptable quality if the scored input data 102 exceeds a majority of the predetermined score thresholds.

If it is determined that the input data 102 is of an acceptable quality, the data quality module 116 may be configured to provide the input data 102 to an aggregation module 118. The aggregation module 118 is configured to receive repeated data inputs, e.g., including input data 102, and to combine the data inputs. The aggregation module 118 may be configured to provide combined data inputs to other components of the system 100. For example, in some implementations the system 100 may include an IoT sensor that receives input data readings every 500 ms. Typically, the system 100 or an optimization task corresponding to the input data readings may only require that input data readings be received every 5 seconds. Therefore, in this example, the aggregation module 118 may be configured to combine and aggregate the input readings in order to generate a simpler, e.g., low dimensional, data input. In some cases this may improve the efficiency of further calculations performed by the system 100.

If it is determined that the input data 102 is not of an acceptable quality the data quality module 116 may be configured to instruct the system 100 to process an alternative data input, e.g., a data input that is an average from previous data inputs or extrapolated from the current data stream. Alternatively, if the accuracy of a particular data input is determined to be critical to the system's ability to perform one or more computations, the data quality module 116 may be configured to enter an error condition. In these examples, the data quality module 116 may learn when and how to instruct the system 100 to process alternative data inputs through a machine learning training process.

Optionally, the multi-state quantum optimization engine 100 may include an analytics platform 126. The analytics platform 126 is configured to process received data, e.g., input data 102 or data representing one or more local or global solutions to an optimization task, and provide analytics and actionable insights relating to the received data.

Optionally, the multi-state quantum optimization engine 100 may include a workflow module 134. The workflow module 134 may be configured to provide a user interface for assigning values to optimization task parameters, defining optimization task objectives, and managing the learning process by which the system 100 may be trained. The workflow module 134 may be further configured to allow for users of the system 100 to coordinate on complex objective-related tasks such that the system 100 may be used efficiently. The workflow module 134 may also be configured to allow for various levels of role-based access controls. For example, the workflow module 134 may be configured to allow a junior team member to modify some of the task objectives, but keeps them from modifying critical ones. In this manner, the workflow module 134 may reduce the likelihood that critical undesirable actions, such as the opening of large water mains in a water network, are avoided.

Figure 2:
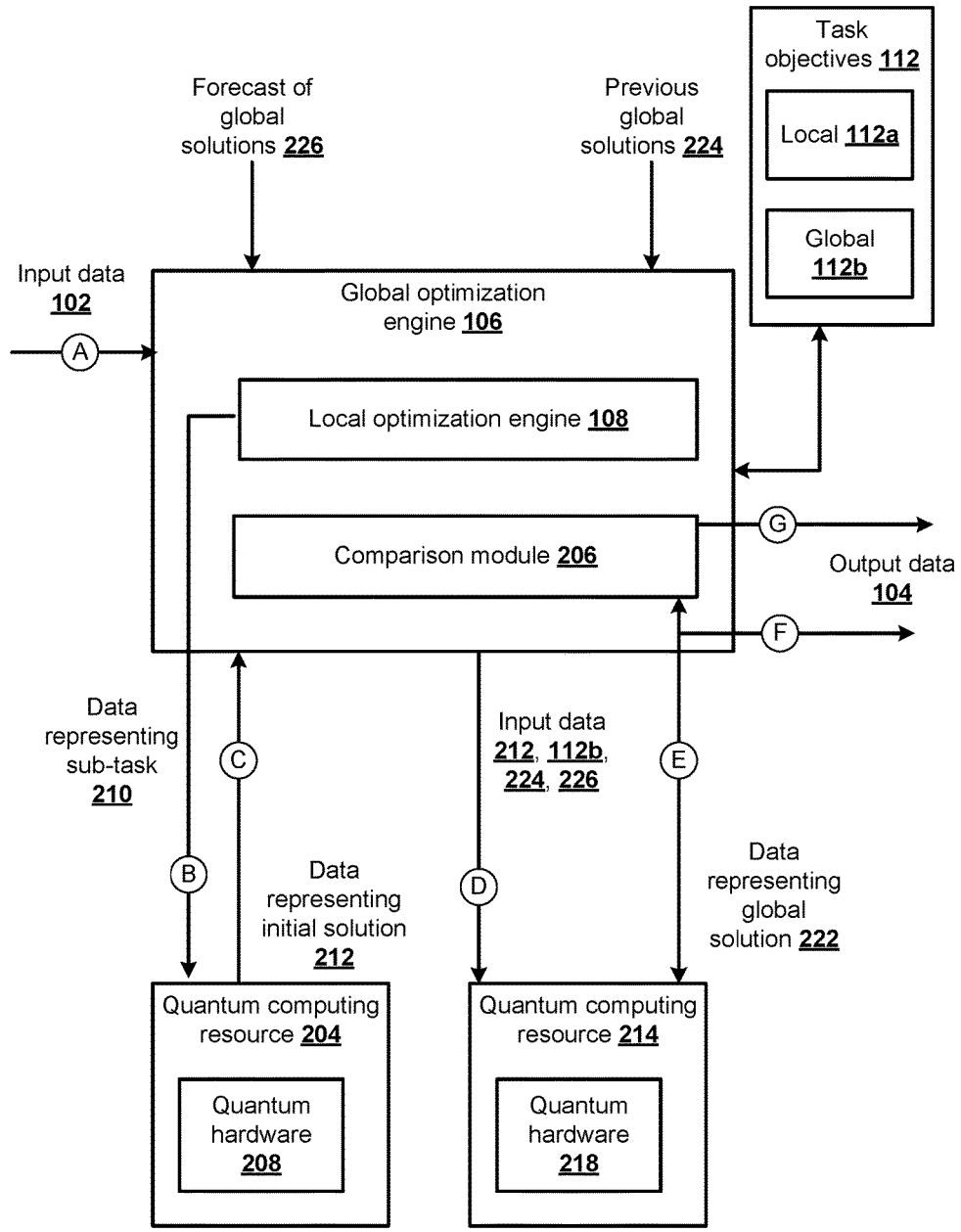
FIG. 2 depicts an example global optimization engine.

FIG. 2 depicts an example global optimization engine 106, as introduced above with reference to FIG. 1A. The example global optimization engine 106 includes a local optimization engine 108 and a comparison module 206. As described above with reference to FIG. 1A, the global optimization engine 106 is in communication with at least one or more additional computing resources, e.g., quantum computing resource 204, and a database storing one or more task objectives, e.g., data store 112.

During operation (A), the global optimization engine 106 is configured to receive input data 102 specifying an optimization task to be solved, together with data representing one or more properties of the optimization task and parameters of the optimization task, as described above with reference to FIG. 1A. The input data may include static data and dynamic data. For example, continuing the example optimization task of optimizing the design of a water network described above with reference to FIG. 1A, during operation (A), the global optimization engine 106 may receive dynamic data representing current readings of water pressures at various locations of the water network, and static data representing fluid dynamical characteristics of the fluid flowing through the network.

In some implementations the global optimization engine 106 may be configured to receive the input data 102 directly, e.g., in a form in which the input data 102 was provided to the multi-state quantum optimization engine 100 as described above with reference to FIG. 1A. In other implementations the global optimization engine 106 may be configured to receive the input data 102 from another component of the multi-state quantum optimization engine 100, e.g., from an integration layer 114 or data quality module 116.

The global optimization engine 106 is configured to provide the received input data 102 to the local optimization engine 108. The local optimization engine 108 is configured to process the input data 102 to obtain one or more initial solutions to the optimization task based on local task objectives 112a included in the task objectives data store 112. As described above with reference to FIG. 1A, initial solutions to the optimization task may include solutions to sub-tasks of the optimization task. For example, initial solutions may include solutions that are optimal over a subset of parameters associated with the optimization task, or, in cases where the optimization task is a separable task that may be written as a sum of sub-tasks, solutions to the sub-tasks.

In some implementations, the local optimization engine 108 may be configured to process the input data 102 to obtain one or more initial solutions to the optimization task by partitioning the optimization task into one or more sub-tasks. For example, as described above with reference to FIG. 1A, the local optimization engine 108 may be in data communication with a subgraph component 122 of the multi-state quantum optimization engine 100, and may be configured to provide the subgraph component 122 with data representing the optimization task, and to receive data representing multiple minimally connected sub graphs representing sub-tasks of the optimization problem. For each sub-task, the local optimization engine 108 may be further configured to identify local task objectives from the task objective data store 112 that are relevant to the sub-task. The local optimization engine 108 may then be configured to route data representing each sub-task with its respective identified local task objectives to respective computing resources included in the system. The computing resources included in the system may process received tasks using a first set of algorithms, e.g., classical or quantum algorithms.

At least one of the obtained one or more initial solutions may be obtained from a quantum computing resource, e.g., quantum computing resource 204. For example, the local optimization engine 108 may be configured to provide data specifying the optimization task and one or more local task objectives 112a to a quantum annealer.

To solve an optimization task using a quantum annealer, e.g., quantum computing resource 204, quantum hardware 208 included in the quantum annealer may be constructed and programmed to encode a solution to the optimization task into an energy spectrum of a many-body quantum Hamiltonian $H_p$ that characterizes the quantum hardware 208. For example, the solution maybe encoded in the ground state of the Hamiltonian $H_p$. The quantum hardware 208 may be configured to perform adiabatic quantum computation starting with an easy to prepare, known ground state of a known initial Hamiltonian $H_i$. Over time, as the known initial Hamiltonian $H_i$ evolves into the Hamiltonian for solving the problem $H_p$, the known ground state evolves and remains in the instantaneous ground state of the evolving Hamiltonian. The ground state of the Hamiltonian $H_p$ is obtained at the end of the evolution. The solution to the optimization task may then be readout by measuring the quantum hardware 208.

During operation (B), the local optimization engine 108 may be configured to provide the quantum annealer with data representing a sub-task of the optimization task 210. For example, the local optimization engine 108 may apply local task objectives to the data received at stage (A), and transmit data representing the complex task to the quantum computing resource 204.

In some implementations the local optimization engine 108 may be configured to communicate with the quantum computing resource 204 to determine physical connectivities and interactions that are available within the quantum hardware 208 in order to map the sub-task to a suitable Hamiltonian $H_p$ that may be implemented by the quantum hardware 208 of the quantum computing resource 204. The local optimization engine 108 may then be configured to provide the quantum computing resource 204 with data representing the Hamiltonian $H_p$. In other implementations, the quantum computing resource 204 may include one or more components that are configured to receive data representing a sub-task and one or more sub-task objectives, and to encode the received data into a suitable Hamiltonian that may be implemented by the quantum hardware 208, e.g., using a quantum compiler.

During operation (C), the global optimization engine 106 is configured to receive data representing the initial solution to the sub-task 212, e.g., a solution set for a local optimization task, from the quantum computing resource 204. The global optimization engine 106 may be configured to make one or more calls to the comparison module 206, reference the global task objectives 112b, or reference static data received during stage (A) of the process to determine a complex global optimization task to send to the quantum computing resource 214. Continuing the example described above, examples of complex global optimization tasks may include the task of determining which actions to take such that, at the end of a given time period, specific water pressures, mixtures, or total accumulated flow rates are achieved, based on current input data, forecast outcomes, historical outcomes and task constraints. Although not shown in FIG. 2, the global optimization engine 106 is further configured to receive data representing initial solutions to other sub-tasks from other computing resources, e.g., additional computing resources 110a-110d, as described above with reference to FIG. 1A.

To generate a global solution to the optimization task, during operation (D) the global optimization engine 106 is configured to provide data representing the one or more initial solutions, e.g., including data representing initial solution 212, and data representing the optimization task to be solved to a second quantum computing resource 214, e.g., a second quantum annealer. The second quantum computing resource 214 may process the received data using a second set of algorithms, e.g., classical or quantum algorithms. In some cases, the second set of algorithms may differ to the first set of algorithms described above. For example, the first set of algorithms may include a first annealing schedule and the second set of algorithms may include a second annealing schedule that is different to the first annealing schedule.

In some implementations, the global optimization engine 106 may be configured to provide additional data to the second quantum computing resource 214. The additional data may include, but is not limited to, data representing global task objectives 112b, data representing previously generated global solutions to previously seen optimization tasks within a predetermined period of time, or data representing a forecast of global solutions to optimization tasks that may be seen during a remainder of the predetermined period of time. For example, the global optimization engine 106 may provide the quantum computing resource with intermediate solutions to the optimization task as part of an iterative process for generating a final solution to the optimization task.

In some implementations the global optimization engine 106 may be configured to communicate with the second quantum computing resource 214, e.g., a second quantum annealer, to determine physical connectivities and interactions that are available within the quantum hardware 218 in order to map the optimization task and additional data 112b, 224 and 226 to a suitable Hamiltonian $H'_p$ that may be implemented by the quantum hardware 218 of the second quantum computing resource 214. The global optimization engine 106 may then be configured to provide the second quantum computing resource 214 with data representing the Hamiltonian $H'_p$. In other implementations, the quantum computing resource 214 may include one or more components that are configured to receive data representing the optimization task and the additional data 212b, 224 and 226, and to encode the received data into a suitable Hamiltonian that may be implemented by the quantum hardware 218, e.g., using a quantum compiler.

The second quantum computing resource 214 may be configured to receive the data representing the one or more initial solutions 212, optimization task to be solved, and additional data 112b, 224, 226, or to receive data representing a suitable Hamiltonian $H'_p$ and to perform a quantum annealing schedule based on the received data in order to determine a global solution to the optimization task.

In some implementations algorithms used by the second quantum computing resource 214 may be varied based on forecasted global solutions. For example, in some cases global task objectives associated with an optimization task may include a target global outcome of the global solution to the optimization task. Continuing the example of optimizing a water network, a target global outcome of a global solution may be that the global solution maximizes an amount of water processed by the network in a given unit of time. The global optimization engine 106 may therefore vary algorithms used by the second quantum computing resource (and/or in some cases vary the type of quantum computing resource) based on the global target outcome, such that the second quantum computing resource 214 processes received initial solutions in a manner that iteratively guides a generated global solution towards the global target outcome.

For example, the quantum multi-state optimization engine may perform a series of local calculations throughout a given time period, e.g., one day, where each local calculation results in outcomes/actions that contribute to achieving a target global outcome at the end of the day. In some settings input data received by the quantum multi-state optimization engine may include dynamic data that changes over time, e.g., dynamic data from IoT. In these settings, a choice of quantum computing resource or an algorithm used by a quantum computing resource at a beginning of the given time period may result in an output that is likely to achieve or contribute towards the target global outcome, however the same choice of quantum computing resource or algorithm used by a quantum computing resource at the end of the given time period may not result in an output that is likely to achieve or contribute towards the target global outcome.

For example, a quantum annealing schedule used by a quantum annealer at the beginning of a given time period may include a first rate of change of transverse field strength or variable representing temperature. The first rate of change may depend on the input data and local solutions generated by the local optimization engine at the beginning of the time period. In some cases, the input data and local solutions generated by the local optimization engine at the end of the time period may differ significantly from the input data and local solutions generated by the local optimization engine at the beginning of the time period. For example, the amount of input data and/or number and complexity of local solutions may be larger. Therefore, to improve accuracy of the global solution obtained by the second quantum computing resource, it may be beneficial to use a quantum annealing schedule with a second rate of change of transverse field strength or variable representing temperature. For example, the second rate of change may be slower than the first rate of change.

During operation (E), the global optimization engine 106 is configured to receive data representing a global solution to the optimization task 222 from the second quantum computing resource 214. In some implementations, during operation (F), the global optimization engine 106 may be configured to directly provide the data representing the global solution to the optimization task as output, e.g., as output data 104. In other implementations, the global optimization engine 106 may be configured to provide the comparison module 206 with the data representing the global solution to the optimization task 222.

The comparison module 206 is configured to compare the data representing the generated global solution to the optimization task 222 with data representing the global task objectives 112b to determine whether the generated global solution 222 sufficiently satisfies the global task objectives 112b. For example, the comparison module 206 may be configured to apply a comparison function to the data representing the generated global solution 222 and the data representing the global task objectives 112b to generate a comparison score. The comparison module 206 may then be configured to compare the comparison score to a predetermined score threshold to determine whether the generated global solution 222 sufficiently satisfies the global task objectives 112b.

During operation (G), if the comparison module 206 determines that the generated global solution 222 sufficiently satisfies the global task objectives 112b, the comparison module may be configured to provide as output 104 data representing the global solution 222 and, optionally data representing the one or more initial solutions as obtained by the local optimization engine 108, e.g., data including data representing initial solution 212.

During operation, if the comparison module 206 determines that the generated global solution 222 does not sufficiently satisfy the global task objectives 112b, the comparison module may be configured to generate modified global optimization engine input data, e.g., a modified version of input data 102. The modified input data may include (i) data specifying the optimization task to be solved, and (ii) modified local task objectives for solving the optimization task. Modified input data includes input data, e.g., input data 102, that has been altered or biased in such a manner that a next iteration of computations performed by the system for solving the optimization task will better align with the global task objectives of the optimization task.

To generate modified global optimization engine input data, the comparison module 206 may be configured to apply deep learning regularization techniques to the current input data to generate biased input data, e.g., biased local task objectives. This may include applying one or more dropout algorithms which selectively block optimization task parameters.

For example, continuing the example optimization task of optimizing the design of a water network, an example optimization task parameter may include a total number of available pipes in the water network. Initially, received input data 102 may include data specifying that there are 2000 pipes available in the water network, whereas data specifying the global task objectives for the optimization task may specify that a maximum of 1000 pipes are to be used. If a generated global solution to the optimization task specifies that 1500 pipes are to be used in an optimal design of the water network, the comparison module may be configured to determine that the generated global solution does not sufficiently satisfy the global task objectives, and may generate modified global optimization engine input data for the optimization task. For example, the comparison module may selectively block or fix one or more optimization task parameters, e.g., including the number of available water pipes. Alternatively or in addition, the comparison module may bias the input data, e.g., bias the input data such that it specifies that there are 1200 pipes available in the water network instead of 2000.

The global optimization engine 106 may be configured to process the modified input data as described above with reference to operations (B)-(E). For example, the global optimization engine 106 may be configured to process the modified input data to obtain one or more modified solutions to the optimization task based on the modified local task objectives. The global optimization engine 106 may then be configured to process the generated one or more modified solutions using the second quantum computing resource 214 to generate a modified global solution to the optimization task based on the global task objectives 112b. When it is determined that a generated global solution sufficiently satisfies the global task objectives 112b, the comparison module 206 may be configured to provide as output 104 data representing the global solution and, optionally data representing the one or more corresponding initial solutions as obtained by the local optimization engine 108. An iterative process for generating a global solution and one or more local solutions to an optimization task is described in more detail below with reference to FIG. 4.

Programming the Hardware

Figure 3:
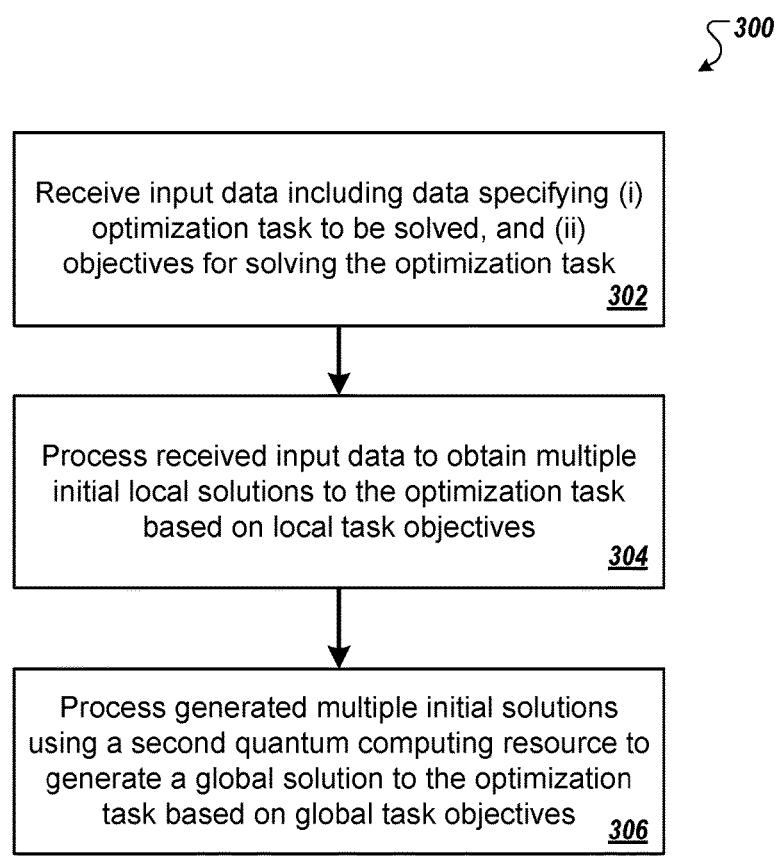
FIG. 3 is a flow diagram of an example process for generating a global solution to an optimization task based on one or more global task objectives.

FIG. 3 is a flowchart of an example process 300 for solving an optimization task using a system including multiple computing resources, where the multiple computing resources include at least one quantum computing resource. For convenience, the process 200 will be described as being performed by a system of one or more classical or quantum computing devices located in one or more locations. For example, an optimization engine, e.g., the multi-state quantum optimization engine 100 of FIG. 1A, appropriately programmed in accordance with this specification, can perform the process 300.

The system receives input data including (i) data specifying the optimization task to be solved, and (ii) data specifying task objectives for solving the optimization task (step 302). The input data may include both static data and dynamic data. The task objectives for solving the optimization task include local task objectives and global task objectives. For example, as described above with reference to FIG. 1A, the optimization task may be the task of optimizing the design of a network, e.g., a water network. In this example, the data specifying the optimization task to be solved may include details about the network, e.g., a total number of available water pipes, connectors or tanks or a total network capacity. Local task objectives may include constraining the values of respective water pressures in each pipe, or constraining the values of a concentration of chemicals in the water. Global task objectives may include constraining an amount of water wastage or specifying a target distributing rate.

As another example, the optimization task may be the task of optimizing a cancer radiotherapy treatment, e.g., minimizing collateral damage of radiotherapy treatment to tissue and body parts surrounding a tumor. In this example, the data specifying the optimization task to be solved may include details about the treatment, e.g., where a tumor is located, types of surrounding tissue, types of surrounding body parts, strength of treatment. Local task objectives may include constraining the strength of the treatment or specifying an area of the body, e.g., the ocular nerve, which should not be affected by the treatment. Global task objectives may include administering a particular amount or strength of treatment. Other example optimization tasks may occur in areas such as machine learning, protein folding, sampling/Monte Carlo, information security, pattern recognition, image analysis, systems design, precision agriculture, scheduling, and bioinformatics.

The system processes the received input data to obtain one or more initial solutions to the optimization task based on the local task objectives, i.e., one or more local solutions (step 304). At least one of the initial solutions is obtained from a first quantum computing resource. As described above with reference to FIGS. 1A and 1B, local solutions to an optimization task may include solutions to sub-tasks of the optimization task. For example, local solutions may include solutions that are optimal over a subset of the parameters associated with the optimization task, e.g., where the subset is specified by the local task objectives. As another example, in cases where the optimization task is a separable task, e.g., a task that may be written as the sum of multiple sub-tasks, local solutions may include optimal solutions to each of the sub-tasks in the sum of sub-tasks, e.g., where the sub-tasks are specified by the local task objectives. In some implementations the local solutions may be probabilistic solutions, e.g., probability distributions over one or more parameters associated with the optimization task.

For example, continuing the first example above, local solutions to the task of optimizing a water network may include optimal values for a subset of parameters associated with the optimization task, e.g., optimal values for water pressures in one or more water pipes, or an optimal concentration of chemicals in the water in the network, or optimal values for all parameters in a portion of the water network. In addition, continuing the second example above, local solutions to the task of optimizing a cancer radiotherapy treatment may include optimal values for a subset of parameters associated with the optimization task, e.g., optimal values for a strength of treatment, or optimal values for all parameters when applied to a specific region of a patient's body.

In some implementations, the system may process the received input data to generate one or more initial local solutions to the optimization task by partitioning the optimization task into one or more sub-tasks. For example, the system may represent the optimization task as a graph of nodes and edges, and partition the graph into multiple minimally connected sub graphs to assist computational processing of the sub-tasks.

The system may then, for each sub-task, identify local task objectives relevant to the sub-task and route (i) the sub-task, and (ii) the identified local task objectives, to respective computing resources included in the system. The system obtains respective solutions to each of the sub-tasks from the respective computing resources included in the system.

The system processes the generated one or more initial solutions using a second quantum computing resource to generate a global solution to the optimization task based on the global task objectives (step 306). As described above with reference to FIG. 1A, a global solution to an optimization task may include parameter values that, when implemented in a system corresponding to the optimization task, provide a highest likelihood that the system achieves the one or more global task objectives. In some implementations, parameter values specified by local solutions to the optimization task may be the same as parameter values specified by a global solution. In other implementations, parameter values specified by local solutions may differ from parameter values specified by a global solution.

In some implementations, the system may process the generated one or more initial local solutions to obtain a global solution to the optimization task based on the global task objectives by processing the generated one or more initial local solutions together with additional data. The additional data may include (i) data representing obtained global solutions to previously received optimization tasks within a predetermined time frame, (ii) data representing a forecast of future received optimization tasks within a remaining predetermined time frame, or (iii) data representing a solution to the optimization task that is independent of the global task objectives. Including such additional data may increase the computational accuracy of the system and produce better global solutions, e.g., when compared to global solutions generated based on one or more initial local solutions and global task objectives only.

In some implementations, the second quantum computing resource may be a quantum annealer. In these implementations, the global solution to the optimization task may be encoded into an energy spectrum of a problem Hamiltonian characterizing the quantum annealer. To generate the global solution, the quantum annealer may follow a quantum annealing schedule based on the one or more initial local solutions, and optionally the additional data.

The generated global solution may be used to determine one or more actions to be taken in a system corresponding to the optimization task, i.e., one or more adjustments to system parameter values. In some cases, adjusting each system parameter may be practically impossible. In these cases it may be more practical to determine one or more local actions to be taken in local areas of the system corresponding to the optimization task, i.e., one or more adjustments to a subset of system parameter values, where the local actions are also based on global task objectives. Generating one or more local solutions to an optimization task based on one or more global task objectives is described in more detail below with reference to FIG. 4.

Figure 4:
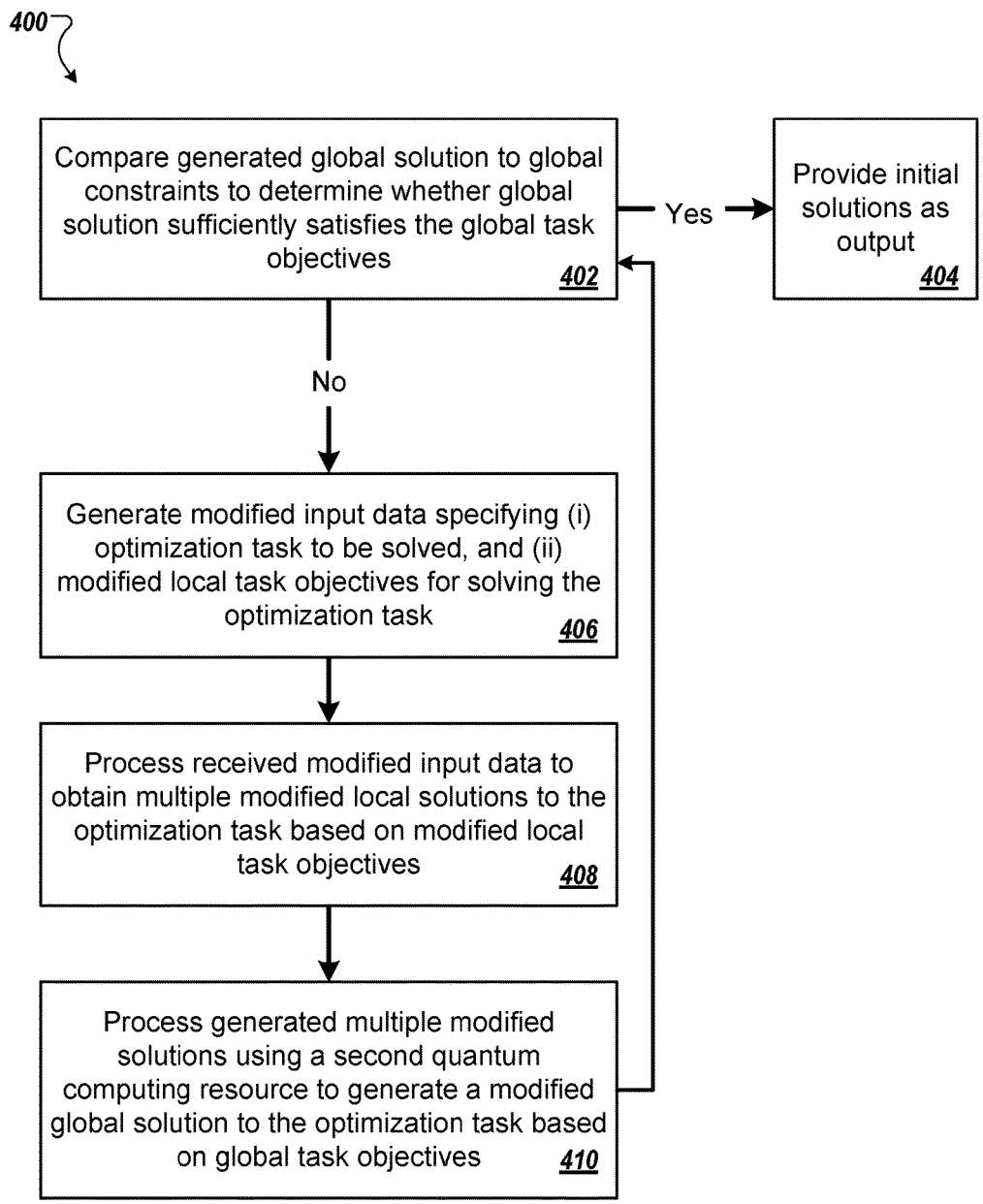
FIG. 4 is a flow diagram of an example iteration of generating one or more local solutions to an optimization task based on one or more global task objectives.

FIG. 4 is a flow diagram of an example iteration of generating one or more local solutions to an optimization task based on one or more global task objectives. For convenience, the process 400 will be described as being performed by a system of one or more classical or quantum computing devices located in one or more locations. For example, an optimization engine, e.g., the multi-state quantum optimization engine 100 of FIG. 1A, appropriately programmed in accordance with this specification, can perform the process 400.

The system compares a generated global solution to the optimization task with the global task objectives to determine whether the generated global solution sufficiently satisfies the global task objectives (step 402). For example, the system may be configured to apply a comparison function to data representing the generated global solution and data representing the global task objectives. Based on the result of the comparison function, the system may score the generated global solution. If the score exceeds a predetermined score threshold, the system may determine whether the global solution sufficiently satisfies the global task objectives or not.

In response to determining that the generated global solution sufficiently satisfies the global task objectives, the system provides as output, data representing the one or more initial solutions to the optimization task (step 404). As described above with respect to FIGS. 1 and 3, data representing the one or more initial solutions to the optimization task may be used to determine one or more actions to take in the system for which the optimization task is specified. For example, the initial solutions may correspond to local task objectives on a subset of optimization task parameters, e.g., a subset of accessible, tunable parameters. Taking actions based on the one or more initial solutions may therefore include adjusting the subset of parameters based on the one or more initial solutions. Due to the specific system architecture and process described above with reference to FIGS. 1-3, taking actions based on the one or more initial solutions enables the system for which the optimization task is defined to achieve or come closer to achieving the global task objectives.

In response to determining that the generated global solution does not sufficiently satisfy the global task objectives, the system generates modified input data comprising (i) data specifying the optimization task to be solved, and (ii) modified local task objectives for solving the optimization task (step 406). Generating modified global optimization engine input data may include applying deep learning regularization techniques to current input data specifying the optimization task and task objectives to generate biased input data, e.g., biased local task objectives. This may include applying one or more dropout algorithms which selectively block optimization task parameters, as described above with reference to FIG. 2.

The system processes the received modified input data to obtain one or more modified solutions to the optimization task based on the modified local task objectives (step 408). For example, the system may perform operations as described with reference to step 304 of FIG. 3 above.

The system processes the generated one or more modified solutions using the second quantum computing resource to generate a modified global solution to the optimization task based on the global task objectives (step 410). For example, the system may perform operations as described with reference to step 306 of FIG. 3 above.

The system may be configured to iteratively perform steps 402-410 until, at step 402, it is determined that the generated global solution for the iteration sufficiently satisfies the global task objectives.

Implementations of the digital and/or quantum subject matter and the digital functional operations and quantum operations described in this specification can be implemented in digital electronic circuitry, suitable quantum circuitry or, more generally, quantum computational systems, in tangibly-embodied digital and/or quantum computer software or firmware, in digital and/or quantum computer hardware, including the structures disclosed in this specification and their structural equivalents, or in combinations of one or more of them. The term "quantum computational systems" may include, but is not limited to, quantum computers, quantum information processing systems, quantum cryptography systems, or quantum simulators.

Implementations of the digital and/or quantum subject matter described in this specification can be implemented as one or more digital and/or quantum computer programs, i.e., one or more modules of digital and/or quantum computer program instructions encoded on a tangible non-transitory storage medium for execution by, or to control the operation of, data processing apparatus. The digital and/or quantum computer storage medium can be a machine-readable storage device, a machine-readable storage substrate, a random or serial access memory device, one or more qubits, or a combination of one or more of them. Alternatively or in addition, the program instructions can be encoded on an artificially-generated propagated signal that is capable of encoding digital and/or quantum information, e.g., a machine-generated electrical, optical, or electromagnetic signal, that is generated to encode digital and/or quantum information for transmission to suitable receiver apparatus for execution by a data processing apparatus.

The terms quantum information and quantum data refer to information or data that is carried by, held or stored in quantum systems, where the smallest non-trivial system is a qubit, i.e., a system that defines the unit of quantum information. It is understood that the term "qubit" encompasses all quantum systems that may be suitably approximated as a two-level system in the corresponding context. Such quantum systems may include multi-level systems, e.g., with two or more levels. By way of example, such systems can include atoms, electrons, photons, ions or superconducting qubits. In many implementations the computational basis states are identified with the ground and first excited states, however it is understood that other setups where the computational states are identified with higher level excited states are possible. The term "data processing apparatus" refers to digital and/or quantum data processing hardware and encompasses all kinds of apparatus, devices, and machines for processing digital and/or quantum data, including by way of example a programmable digital processor, a programmable quantum processor, a digital computer, a quantum computer, multiple digital and quantum processors or computers, and combinations thereof. The apparatus can also be, or further include, special purpose logic circuitry, e.g., an FPGA (field programmable gate array), an ASIC (application-specific integrated circuit), or a quantum simulator, i.e., a quantum data processing apparatus that is designed to simulate or produce information about a specific quantum system. In particular, a quantum simulator is a special purpose quantum computer that does not have the capability to perform universal quantum computation. The apparatus can optionally include, in addition to hardware, code that creates an execution environment for digital and/or quantum computer programs, e.g., code that constitutes processor firmware, a protocol stack, a database management system, an operating system, or a combination of one or more of them.

A digital computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a digital computing environment. A quantum computer program, which may also be referred to or described as a program, software, a software application, a module, a software module, a script, or code, can be written in any form of programming language, including compiled or interpreted languages, or declarative or procedural languages, and translated into a suitable quantum programming language, or can be written in a quantum programming language, e.g., QCL or Quipper.

A digital and/or quantum computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A digital and/or quantum computer program can be deployed to be executed on one digital or one quantum computer or on multiple digital and/or quantum computers that are located at one site or distributed across multiple sites and interconnected by a digital and/or quantum data communication network. A quantum data communication network is understood to be a network that may transmit quantum data using quantum systems, e.g. qubits. Generally, a digital data communication network cannot transmit quantum data, however a quantum data communication network may transmit both quantum data and digital data.

The processes and logic flows described in this specification can be performed by one or more programmable digital and/or quantum computers, operating with one or more digital and/or quantum processors, as appropriate, executing one or more digital and/or quantum computer programs to perform functions by operating on input digital and quantum data and generating output. The processes and logic flows can also be performed by, and apparatus can also be implemented as, special purpose logic circuitry, e.g., an FPGA or an ASIC, or a quantum simulator, or by a combination of special purpose logic circuitry or quantum simulators and one or more programmed digital and/or quantum computers.

For a system of one or more digital and/or quantum computers to be "configured to" perform particular operations or actions means that the system has installed on it software, firmware, hardware, or a combination of them that in operation cause the system to perform the operations or actions. For one or more digital and/or quantum computer programs to be configured to perform particular operations or actions means that the one or more programs include instructions that, when executed by digital and/or quantum data processing apparatus, cause the apparatus to perform the operations or actions. A quantum computer may receive instructions from a digital computer that, when executed by the quantum computing apparatus, cause the apparatus to perform the operations or actions.

Digital and/or quantum computers suitable for the execution of a digital and/or quantum computer program can be based on general or special purpose digital and/or quantum processors or both, or any other kind of central digital and/or quantum processing unit. Generally, a central digital and/or quantum processing unit will receive instructions and digital and/or quantum data from a read-only memory, a random access memory, or quantum systems suitable for transmitting quantum data, e.g. photons, or combinations thereof.

The essential elements of a digital and/or quantum computer are a central processing unit for performing or executing instructions and one or more memory devices for storing instructions and digital and/or quantum data. The central processing unit and the memory can be supplemented by, or incorporated in, special purpose logic circuitry or quantum simulators. Generally, a digital and/or quantum computer will also include, or be operatively coupled to receive digital and/or quantum data from or transfer digital and/or quantum data to, or both, one or more mass storage devices for storing digital and/or quantum data, e.g., magnetic, magneto-optical disks, optical disks, or quantum systems suitable for storing quantum information. However, a digital and/or quantum computer need not have such devices.

Digital and/or quantum computer-readable media suitable for storing digital and/or quantum computer program instructions and digital and/or quantum data include all forms of non-volatile digital and/or quantum memory, media and memory devices, including by way of example semiconductor memory devices, e.g., EPROM, EEPROM, and flash memory devices; magnetic disks, e.g., internal hard disks or removable disks; magneto-optical disks; CD-ROM and DVD-ROM disks; and quantum systems, e.g., trapped atoms or electrons. It is understood that quantum memories are devices that can store quantum data for a long time with high fidelity and efficiency, e.g., light-matter interfaces where light is used for transmission and matter for storing and preserving the quantum features of quantum data such as superposition or quantum coherence.

Control of the various systems described in this specification, or portions of them, can be implemented in a digital and/or quantum computer program product that includes instructions that are stored on one or more non-transitory machine-readable storage media, and that are executable on one or more digital and/or quantum processing devices. The systems described in this specification, or portions of them, can each be implemented as an apparatus, method, or system that may include one or more digital and/or quantum processing devices and memory to store executable instructions to perform the operations described in this specification.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for solving an optimization task using a system including multiple computing resources, the method comprising:
   receiving input data comprising (i) data specifying system parameters of the optimization task to be solved, and (ii) data specifying task objectives for solving the optimization task, comprising one or more local task objectives and one or more global task objectives;
   processing, by a local optimization engine, the received input data to obtain one or more initial solutions to the optimization task based on the local task objectives, comprising:
      transmitting, using a router, from the local optimization engine and to a first quantum computing resource, (i) the received data specifying the optimization task to be solved, and (ii) data representing one or more of the local task objectives, the router determining which computations to outsource to the first quantum computing resource; and
      receiving, from the first quantum computing resource and at the local optimization engine, data representing an initial solution to the optimization task; and
   processing, by a global optimization engine, the generated one or more initial solutions using a second quantum computing resource to generate a global solution to the optimization task based on the global task objectives, comprising:
      transmitting, from the global optimization engine and to the second quantum computing resource, (i) data representing the one or more obtained initial solutions to the optimization task, and (ii) the received data specifying the optimization task to be solved, and (iii) data representing the one or more global task objectives; and
      receiving, from the second quantum computing resource and at the global optimization engine, data representing the global solution to the optimization task;
   comparing, using a comparison module, the data representing the global solution to the one or more global task objectives to determine whether the global solution satisfies the one or more global task objectives; and
   adjusting values of the system parameters using the generated global solution to the optimization task.

2. The method of claim 1, further comprising comparing, by a comparison module, the generated global solution to the optimization task with the global task objectives to determine whether the generated global solution sufficiently satisfies the global task objectives.

3. The method of claim 2, further comprising:
   in response to determining that the generated global solution sufficiently satisfies the global task objectives, providing as output data representing the one or more initial solutions to the optimization task.

4. The method of claim 2, further comprising, in response to determining that the generated global solution does not sufficiently satisfy the global task objectives:
   generating, by the comparison module, modified input data comprising (i) data specifying the optimization task to be solved, and (ii) modified local task objectives for solving the optimization task;
   processing, by the local optimization engine, the received modified input data to obtain one or more modified solutions to the optimization task based on the modified local task objectives; and
   processing, by the global optimization engine, the generated one or more modified solutions using the second quantum computing resource to generate a modified global solution to the optimization task based on the global task objectives.

5. The method of claim 4, wherein generating modified input data comprises applying deep learning regularization techniques to the received input data to generate biased input data.

6. The method of claim 1, wherein processing the received input data to generate one or more initial local solutions to the optimization task comprises:
   partitioning, by a subgraph module, the optimization task into one or more sub-tasks; and
   for each sub-task:
      identifying local task objectives relevant to the sub-task;
      routing (i) the sub-task, and (ii) the identified local task objectives to respective computing resources included in the system; and
      obtaining a respective solution to the sub-tasks from the respective computing resources included in the system.

7. The method of claim 6, wherein partitioning the optimization task into one or more sub-tasks comprises representing the optimization task as a graph and partitioning the graph into minimally connected sub graphs.

8. The method of claim 6, wherein processing the generated one or more initial local solutions to obtain a global solution to the optimization task based on the global task objectives further comprises processing, by the global optimization engine, the generated one or more initial local solutions and additional data comprising one or more of:
   (i) data representing obtained global solutions to previously received optimization tasks within a predetermined time frame,
   (ii) data representing a forecast of future received optimization tasks within a remaining predetermined time frame, (iii) data representing a solution to the optimization task that is independent of the global task objectives, to obtain the global solution to the optimization task based on the global task objectives.

9. The method of claim 8, wherein the second quantum computing resource is a quantum annealer.

10. The method of claim 9, wherein the global solution to the optimization task based on the global task objectives is encoded into an energy spectrum of a problem Hamiltonian characterizing the quantum annealer.

11. The method of claim 10, wherein processing the generated one or more initial local solutions to obtain a global solution to the optimization task comprises performing a quantum annealing schedule task based on at least the data representing a forecast of future received optimization tasks within a remaining predetermined time frame.

12. The method of claim 1, wherein
processing the received input data to obtain one or more initial solutions to the optimization task based on the local task objectives comprises performing a first set of algorithms;
processing the generated one or more initial solutions using the second quantum computing resource to generate a global solution to the optimization task based on the global task objectives comprises performing a second set of algorithms; and
the first set of algorithms is different to the second set of algorithms.

13. The method of claim 1, wherein the initial solutions to the optimization task comprise probabilistic solutions to the optimization task.

14. The method of claim 1, wherein the received input data specifying task objectives for solving the optimization task comprise static data and real-time data.

15. The method of claim 1, wherein the local optimization engine is configured to communicate with the first quantum computing resource to:
determine physical connectivities and interactions that are available within the first quantum computing resource; and
use the determined physical connectivities and interactions to map the data specifying the optimization task to a Hamiltonian that may be implemented by the first quantum computing resource.

16. A system of multiple computing resources, comprising:
one or more classical processors; and
quantum computing resources;
wherein the one or more classical processors and the quantum computing resources are configured to perform operations comprising:
receiving input data comprising (i) data specifying system parameters of the optimization task to be solved, and (ii) data specifying task objectives for solving the optimization task, comprising one or more local task objectives and one or more global task objectives;
processing, by a local optimization engine, the received input data to obtain one or more initial solutions to the optimization task based on the local task objectives, comprising:
transmitting, using a router, from the local optimization engine and to a first quantum computing resource, (i) the received data specifying the optimization task to be solved, and (ii) data representing one or more of the local task objectives, the router determining which computations to outsource to the first computing resource; and
receiving, from the first quantum computing resource and at the local optimization engine, data representing an initial solution to the optimization task; and
processing, by a global optimization engine, the generated one or more initial solutions using a second quantum computing resource to generate a global solution to the optimization task based on the global task objectives, comprising:
transmitting, from the global optimization engine and to the second quantum computing resource, (i) data representing the one or more obtained initial solutions to the optimization task, and (ii) the received data specifying the optimization task to be solved, and (iii) data representing the one or more global task objectives; and
receiving, from the second quantum computing resource and at the global optimization engine, data representing the global solution to the optimization task;
comparing, using a comparison module, the data representing the global solution to the one or more global task objectives to determine whether the global solution satisfies the one or more global task objectives; and
adjusting values of the system parameters using the generated global solution to the optimization task.

17. The system of claim 16, wherein the two or more quantum computing resources comprise one or more of (i) quantum gate computers, (ii) quantum annealers, or (iii) quantum simulators.

18. The system of claim 17, wherein the second quantum computing resource is a quantum annealer.

19. The system of claim 16, wherein the operations further comprise comparing the generated global solution to the optimization task with the global task objectives to determine whether the generated global solution sufficiently satisfies the global task objectives.

20. The system of claim 19, wherein the operations further comprise:
in response to determining that the generated global solution sufficiently satisfies the global task objectives, providing as output data representing the one or more initial solutions to the optimization task.

21. The system of claim 19, wherein the operations further comprise, in response to determining that the generated global solution does not sufficiently satisfy the global task objectives:
generating modified input data comprising (i) data specifying the optimization task to be solved, and (ii) modified local task objectives for solving the optimization task;
processing the received modified input data to obtain one or more modified solutions to the optimization task based on the modified local task objectives; and
processing the generated one or more modified solutions using the second quantum computing resource to generate a modified global solution to the optimization task based on the global task objectives.

* * * * *

UNITED STATES PATENT AND TRADEMARK OFFICE
CERTIFICATE OF CORRECTION

| | |
|---|---|
| PATENT NO. | : 10,095,981 B1 |
| APPLICATION NO. | : 15/466342 |
| DATED | : October 9, 2018 |
| INVENTOR(S) | : Daniel Garrison, Andrew E. Fano and Jurgen Albert Weichenberger |

Page 1 of 1

It is certified that error appears in the above-identified patent and that said Letters Patent is hereby corrected as shown below:

On the Title Page

Column 2, Line 19, delete "contrainopt.pdf>" and insert -- constrainopt.pdf> --, therefor.

Signed and Sealed this
Second Day of April, 2019

Andrei Iancu
*Director of the United States Patent and Trademark Office*